United States Patent
Usami et al.

(10) Patent No.: US 8,243,172 B2
(45) Date of Patent: Aug. 14, 2012

(54) IMAGE PICKUP SYSTEM

(75) Inventors: Hiroyuki Usami, Kokubunji (JP);
Yutaka Fujisawa, Hino (JP)

(73) Assignee: Olympus Medical Systems Corp.,
Tokyo (JP)

( * ) Notice: Subject to any disclaimer, the term of this patent is extended or adjusted under 35 U.S.C. 154(b) by 587 days.

(21) Appl. No.: 12/427,326

(22) Filed: Apr. 21, 2009

(65) Prior Publication Data

US 2009/0256934 A1    Oct. 15, 2009

(30) Foreign Application Priority Data

Oct. 29, 2007   (JP) ................................ 2007-280632

(51) Int. Cl.
*H04N 5/217* (2006.01)
(52) U.S. Cl. ......... 348/241; 348/222.1; 348/65; 348/73; 348/74; 348/76; 348/192; 348/193; 348/223.1; 348/228.1; 348/230.1; 600/101; 600/109; 600/118; 600/160; 382/128; 382/203
(58) Field of Classification Search .................. 348/241, 348/222.1, 65, 73, 74, 76, 192, 193, 223.1, 348/228.1, 230.1; 600/101, 109, 118, 160; 382/128, 203
See application file for complete search history.

(56) References Cited

U.S. PATENT DOCUMENTS

| 7,728,876 | B2 * | 6/2010 | Sakurai et al. ............. 348/222.1 |
| 2004/0085442 | A1 * | 5/2004 | Kawata ......................... 348/65 |

FOREIGN PATENT DOCUMENTS

JP    06-326916    11/1994

* cited by examiner

*Primary Examiner* — Evelyn A. Lester
(74) *Attorney, Agent, or Firm* — Scully, Scott, Murphy & Presser, P.C.

(57) ABSTRACT

An SSG circuit section is composed of: a memory storing correction information for correcting a transmission characteristic of an image pickup signal in a transmission path; a readout circuit for reading out the correction information stored in the memory; and an SSG for generating a drive signal to be outputted from a driving circuit and a sampling pulse to be used in a CDS circuit, and for specifying an amplification factor of an amplifier circuit.

9 Claims, 10 Drawing Sheets

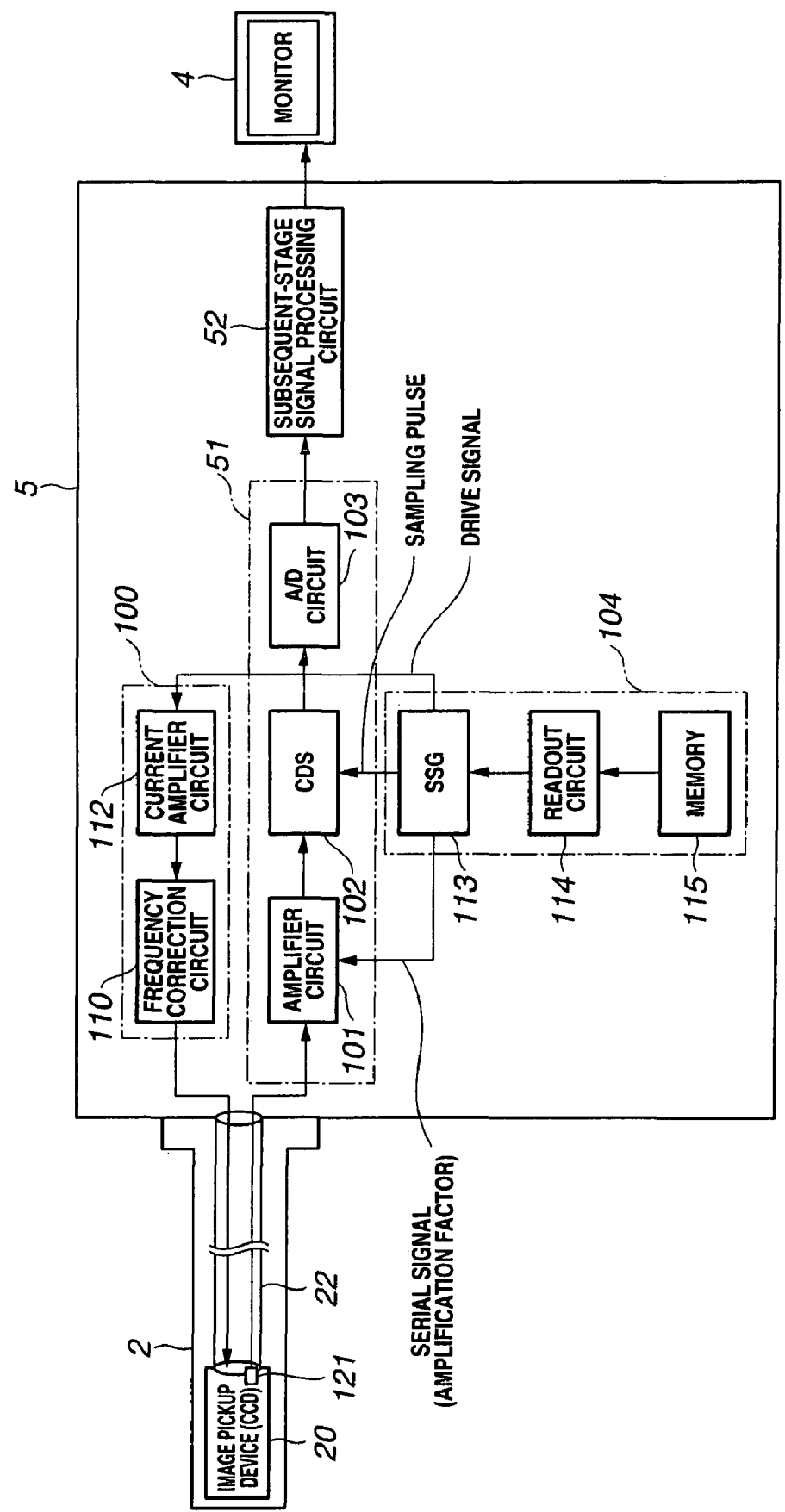

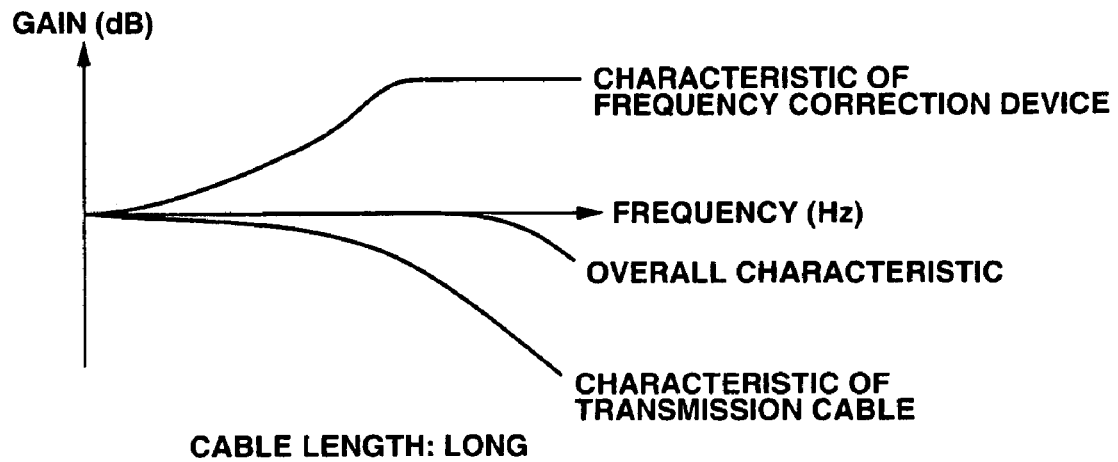
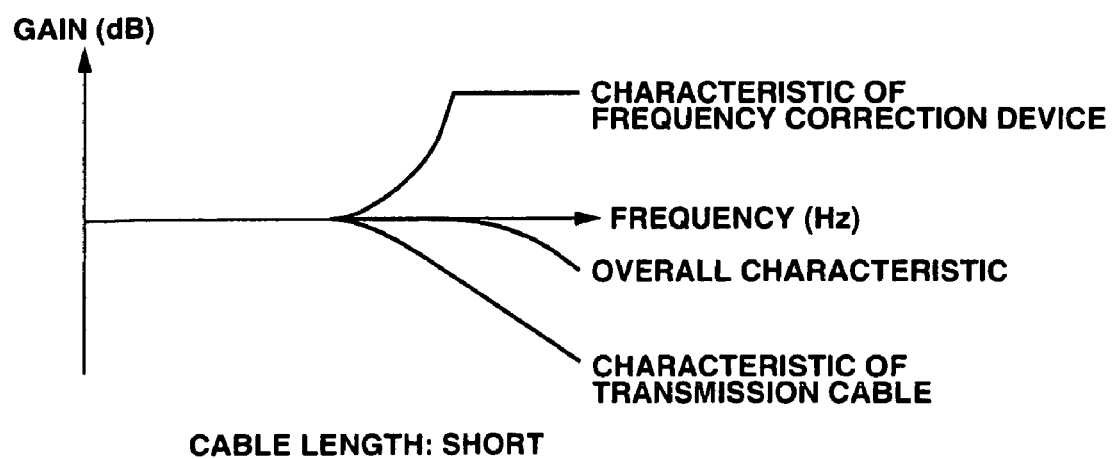

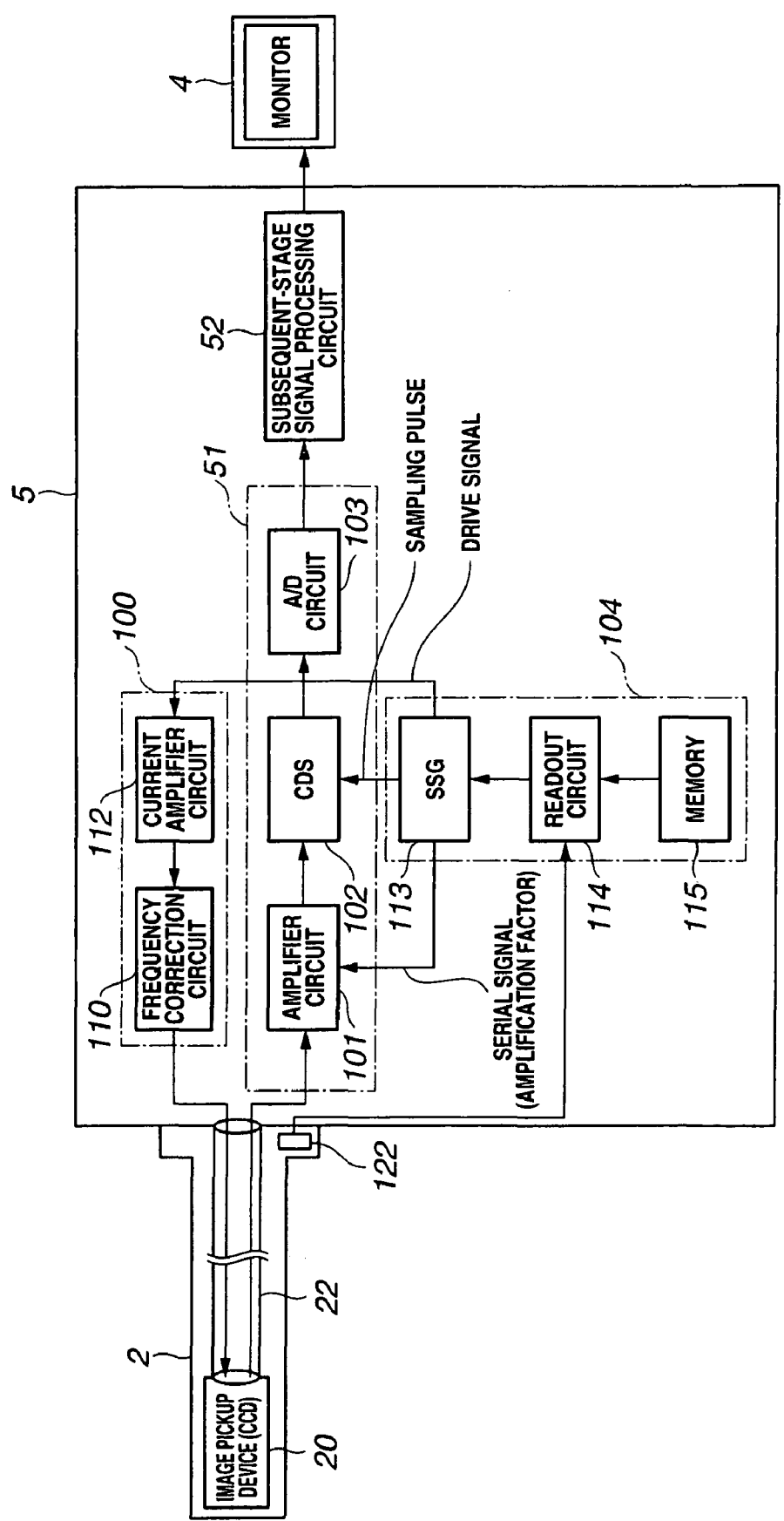

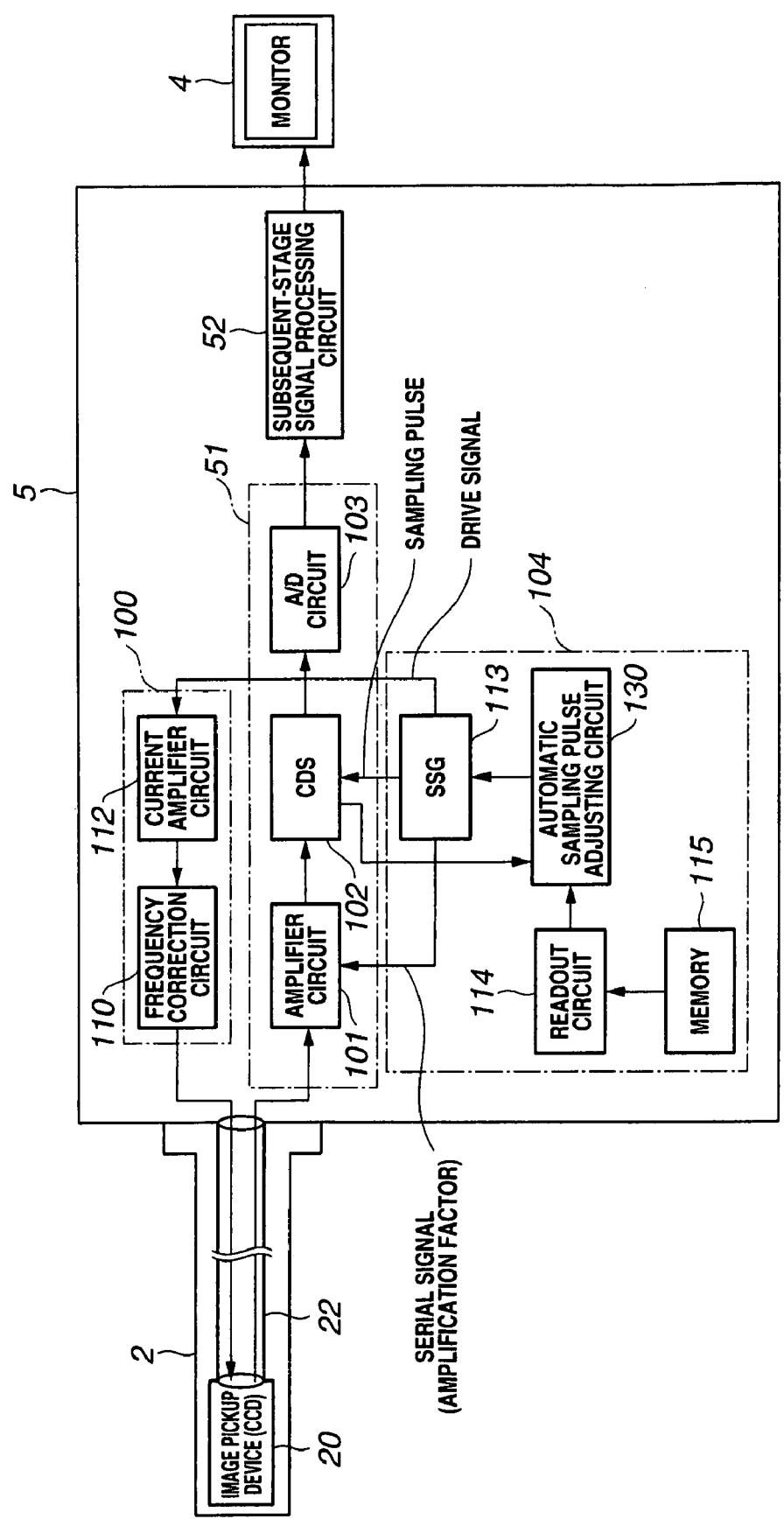

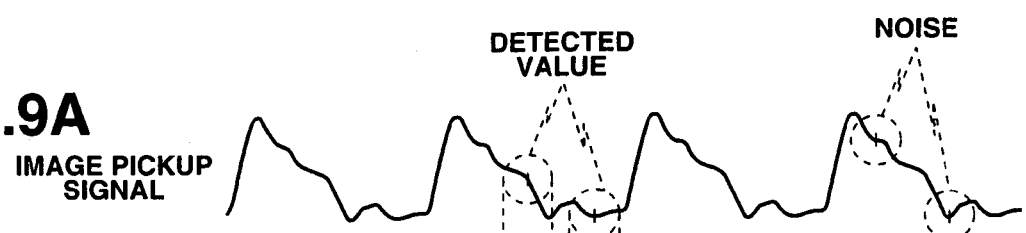
FIG.9A IMAGE PICKUP SIGNAL
FIG.9B SHP
FIG.9C SHD
FIG.10
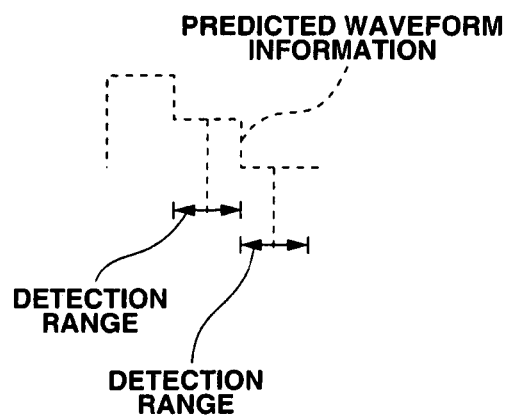

FIG.12
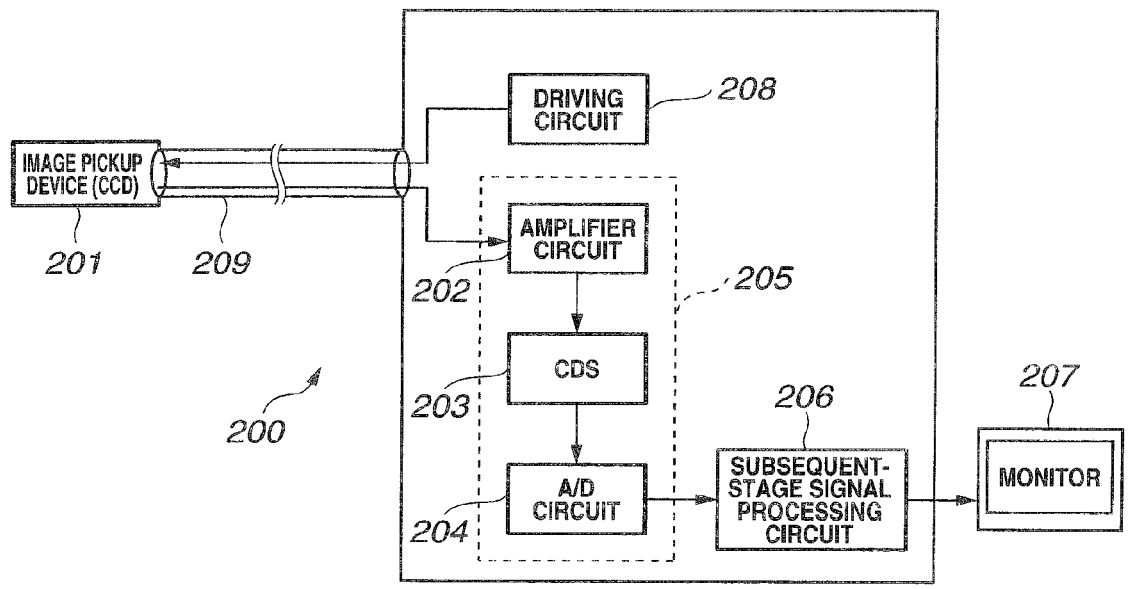
--Prior Art--
FIG.13A IMAGE PICKUP SIGNAL
FIG.13B SHP
FIG.13C SHD
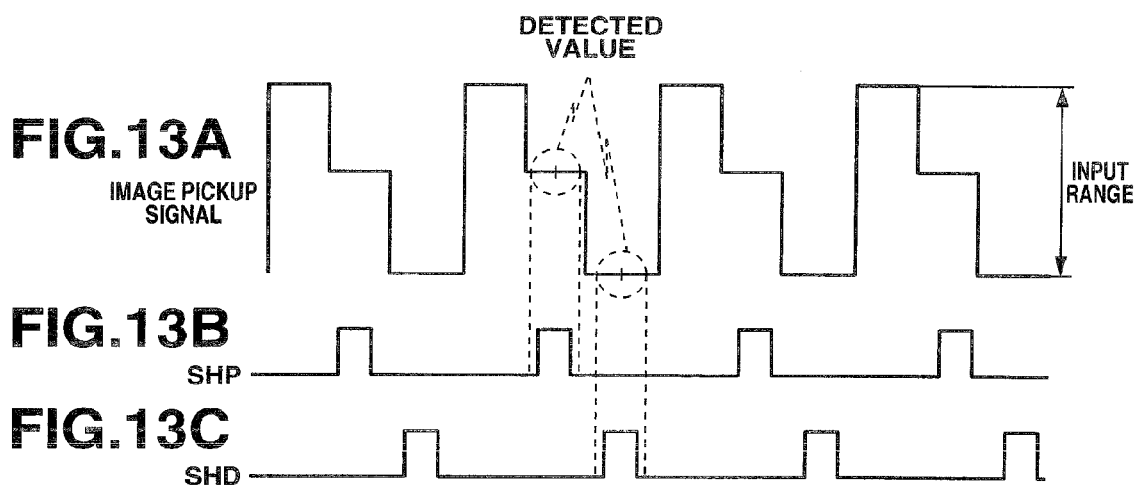
--Prior Art--

IMAGE PICKUP SYSTEM

BACKGROUND OF THE INVENTION

1. Field of the Invention

The present invention relates to an image pickup system for driving an image pickup device that picks up an image of a subject and for signal-processing an image pickup signal.

2. Description of the Related Art

In recent years, various endoscope apparatuses using a solid-state image pickup device such as a charge coupled device (CCD) are proposed.

For example, as shown in FIG. 12, an endoscope apparatus 200 includes: an image pickup section 201 composed of an image pickup device (CCD) for picking up an image of a subject; a preceding-stage signal processing circuit 205 including a CDS circuit 203 for performing correlated double sampling (CDS) on an image pickup signal outputted from the image pickup section 201 and amplified in the amplifier circuit 202 and removing CCD noise, and an A/D circuit 204 for converting an analog image pickup signal into a digital signal; a subsequent-stage signal processing circuit 206 for performing gamma correction, white balance processing, or the like; a driving circuit 208 for driving the image pickup device of the image pickup section 201; a transmission path 209 connecting the image pickup device of the image pickup section 201 and the preceding-stage signal processing circuit 205; and a monitor 207 for receiving a video signal from the subsequent-stage signal processing circuit 206 and displaying an image of a subject.

In such an endoscope apparatus 200, cables with different lengths are used, depending on the product types of endoscopes, as the transmission path 209 for transmitting an image pickup signal from the image pickup device of the image pickup section 201 to the preceding-stage signal processing circuit 205 and also transmitting a drive signal from the driving circuit 208 to the image pickup device of the image pickup section 201. As is known, the lengths of the cables cause difference in attenuation amount at the time of transmitting signals. The longer the cable is, the larger the attenuation rate is.

In addition, in the preceding-stage signal processing circuit 205, as shown in FIGS. 13A to 13C, when inputting an image pickup signal to the CDS circuit 203, it is necessary to adjust the gain of the amplifier circuit 202 such that the image pickup signal is amplified as much as possible to an extent not to exceed the input range. However, due to the difference in the attenuation rates caused by the difference in the cable lengths, it is impossible to adjust the gain to maintain a constant level. Also at the time of sampling, the phase of the image pickup signal is shifted due to the difference in the cable lengths. Accordingly, it is necessary to set the gain of the amplifier circuit 202 and the phases of the sampling pulses SHP and SHD in the CDS circuit 203 for each product type of endoscopes.

In order to solve such a problem, for example, Japanese Patent Application Laid-Open Publication No. 06-326916 discloses a technique in which the length of a cable is discriminated with discrimination means for discriminating the cable length and gain is adjusted by an amplifier section by selecting a resistor corresponding to the cable length, thereby changing the amplification factor.

SUMMARY OF THE INVENTION

An image pickup system according to one aspect of the present invention includes: an image pickup section including an image pickup device for picking up an image of a subject; a signal processing section for signal-processing an image pickup signal outputted from the image pickup device; a transmission path for transmitting the image pickup signal from the image pickup device to the signal processing section; a storage section for storing a correction value corresponding to a characteristic of the image pickup device or a characteristic of the transmission path; and a correction section for electrically correcting the image pickup signal which is signal-processed in the signal processing section, based on the correction value stored in the storage section.

BRIEF DESCRIPTION OF THE DRAWINGS

FIG. 4 is a configurational view showing a configuration of a first modified example of the endoscope apparatus of FIG. 1.

FIG. 5 is a first view describing a characteristic of a frequency correction device of FIG. 4.

FIG. 6 is a second view describing a characteristic of the frequency correction device of FIG. 4.

FIG. 7 is a configurational view showing a configuration of a second modified example of the endoscope apparatus of FIG. 1.

FIG. 8 is a block diagram showing a configuration of a video processor according to a second embodiment of the present invention.

FIGS. 9A to 9C are first views for describing a working of the video processor of FIG. 8.

FIG. 10 is a second view showing the working of the video processor of FIG. 8.

FIG. 12 is a configurational view showing a configuration of a conventional endoscope apparatus.

FIGS. 13A to 13C are views for describing an image pickup signal in a preceding-stage signal processing circuit of FIG. 12.

DETAILED DESCRIPTION OF THE PREFERRED EMBODIMENTS

An image pickup system according to each of the embodiments of the present invention optimally performs amplification and correlated double sampling processing of an image pickup signal by storing predetermined information in a memory.

Conventional endoscope apparatuses have used a technique in which a circuit for measuring characteristics is mounted in order to perform appropriate amplification and sampling on an image pickup signal transmitted through a cable with a length different for each product type of endoscopes and determination of the characteristic is made using the circuit. However, there has been a problem that the circuit scale is large and the configuration thereof is complex.

In contrast, to an image pickup system according to each of the embodiments of the present invention is mounted a storage device (memory) which stores the characteristics previously measured for each product, in order to save the space. Accordingly, the image pickup system enables appropriate amplification and sampling without a measuring circuit.

Each of the embodiments of the present invention enables an optimal processing of an image pickup signal which has been conventionally performed with a large-scale circuit, while ensuring space savings.

Hereinafter, the embodiments of the present invention will be described with reference to the drawings.

First Embodiment

FIGS. 1 to 7 relate to the first embodiment of the present invention.

(Configuration)

Figure 1:
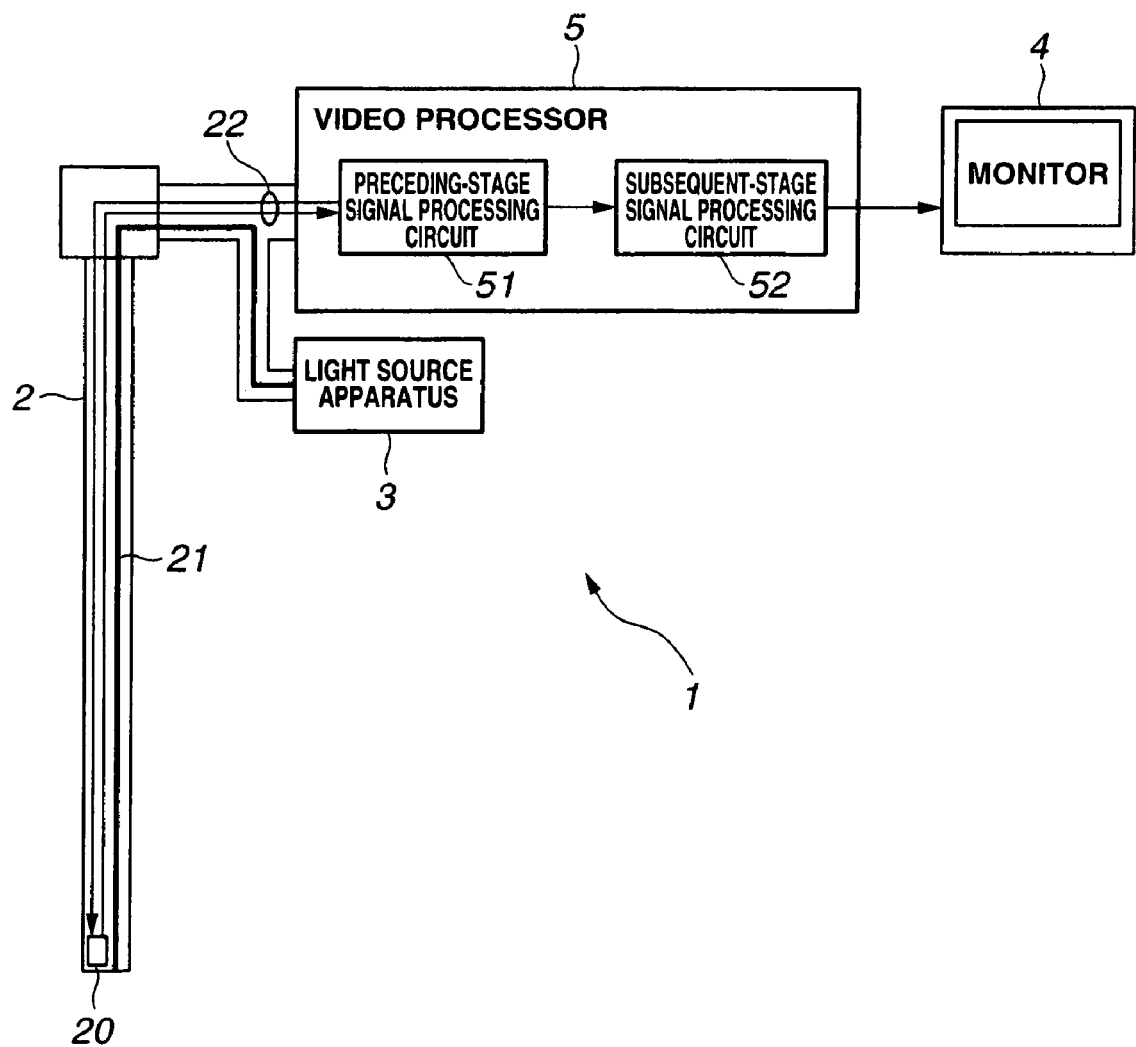
FIG. 1 a configurational view showing a configuration of an endoscope apparatus according to a first embodiment of the present invention.

As shown in FIG. 1, an endoscope apparatus 1 as an image pickup system of the present embodiment is configured by including: an endoscope 2 provided with an image pickup section 20 as image pickup means having an image pickup device (CCD) to be inserted into a body cavity to pick up an image of a subject; a light source apparatus 3 for supplying illumination light to a light guide 21 inserted in the endoscope 2; and a video processor 5, which is connected to the image pickup section 20 through a cable as a transmission path 22, for driving the image pickup section 20 and signal-processing an image pickup signal from the image pickup section 20 to display an image of the subject on a monitor 4. The image pickup section 20 is arranged at a distal end of an insertion portion of the endoscope 2.

Figure 2:
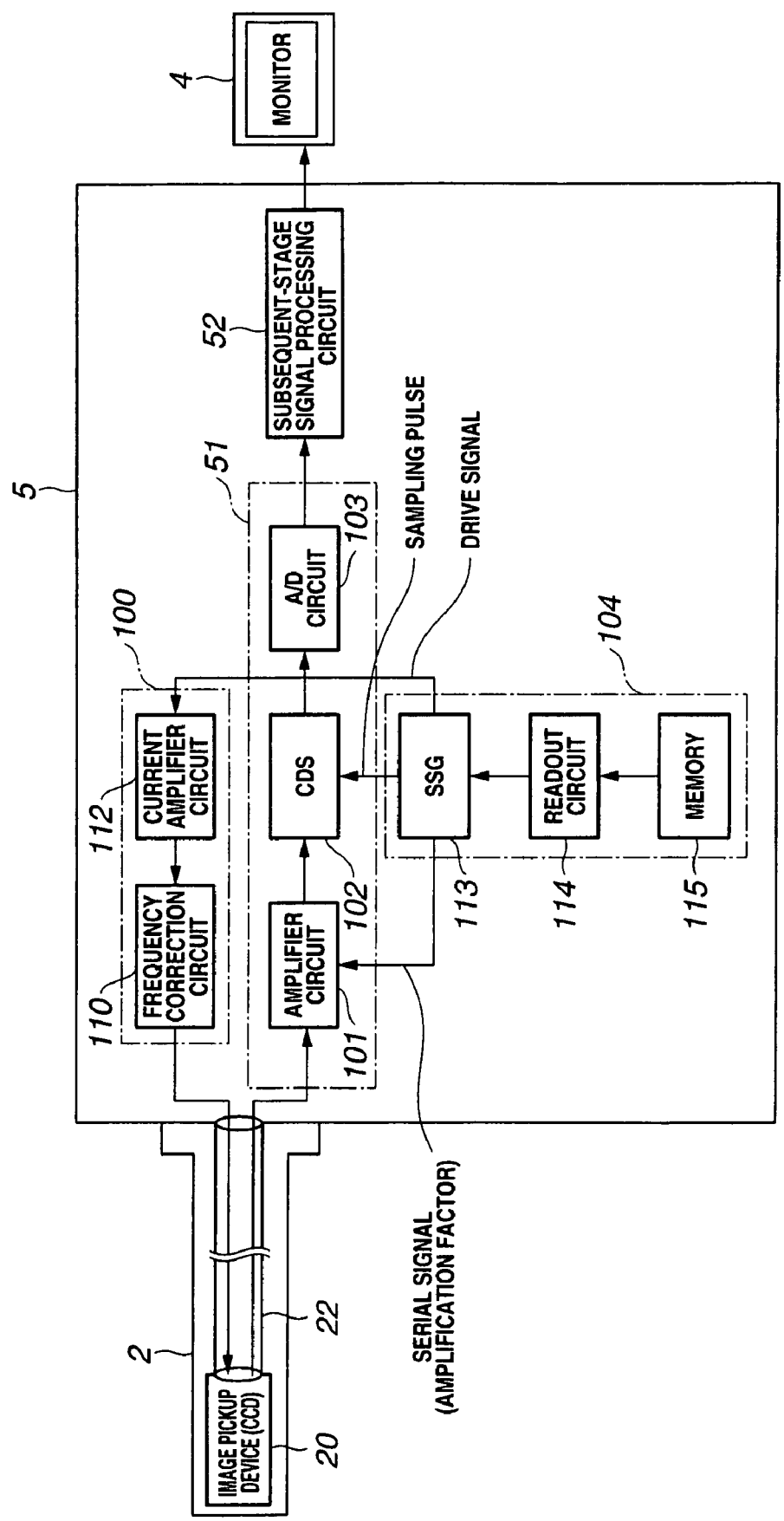
FIG. 2 is a block diagram showing a configuration of a video processor of FIG. 1.

As shown in FIG. 2, the video processor 5 is configured by including: a preceding-stage signal processing circuit 51 as a signal processing section which includes a CDS circuit 102 for performing correlated double sampling (CDS) on the image pickup signal inputted from the image pickup section 20 through an amplifier circuit 101 as an amplifier section and removing CCD noise, and an A/D circuit 103 for converting an analog image pickup signal into a digital signal; and a subsequent-stage signal processing circuit 52 for performing gamma correction, white balance processing, and the like; a driving circuit 100 for driving the image pickup device of the image pickup section 20; and a synchronization signal generator circuit section (hereinafter referred to as SSG circuit section) 104.

The SSG circuit section 104 is configured of a memory 115 as a storage section storing correction information for correcting an image pickup signal-transmission characteristic of the transmission path 22; a readout circuit 114 for reading out the correction information stored in the memory 115; a synchronization signal generator (hereinafter referred to as SSG) 113 for generating a drive signal to be outputted from the driving circuit 100 and sampling pulses (SHP, SHD, ADCLK) to be used in the CDS circuit 102, and specifying an amplification factor of the amplifier circuit 101.

Note that, in the present embodiment, correction means as a correction section is configured of the SSG 113 and the readout circuit 114.

Based on the correction information read out by the readout circuit 114, the SSG 113 specifies or sets the amplification factor of the amplifier circuit 101 by an amplification factor specifying signal as a serial signal, and generates sampling pulses the phases of which are corrected, to output the phase-corrected sampling pulses to the CDS circuit 102. In the memory 115 is stored correction information including correction values corresponding to the characteristic of the image pickup device or the characteristic of the transmission path 22.

The driving circuit 100 as a driving section is configured by including: a current amplifier circuit 112 for amplifying the drive signal from the SSG 113; and a frequency correction circuit 110 for applying phase correction to the drive signal amplified by the current amplifier circuit 112.

(Working)

Description will be made on the working of the endoscope apparatus 1 thus configured according to the present embodiment. Note that in the present embodiment, the correction information stored in the memory 115 is composed of amplification factor information for specifying the amplification factor of the amplifier circuit 101 and phase information for correcting the phases of the sampling pulses to be used in the CDS circuit 102.

Figure 3:
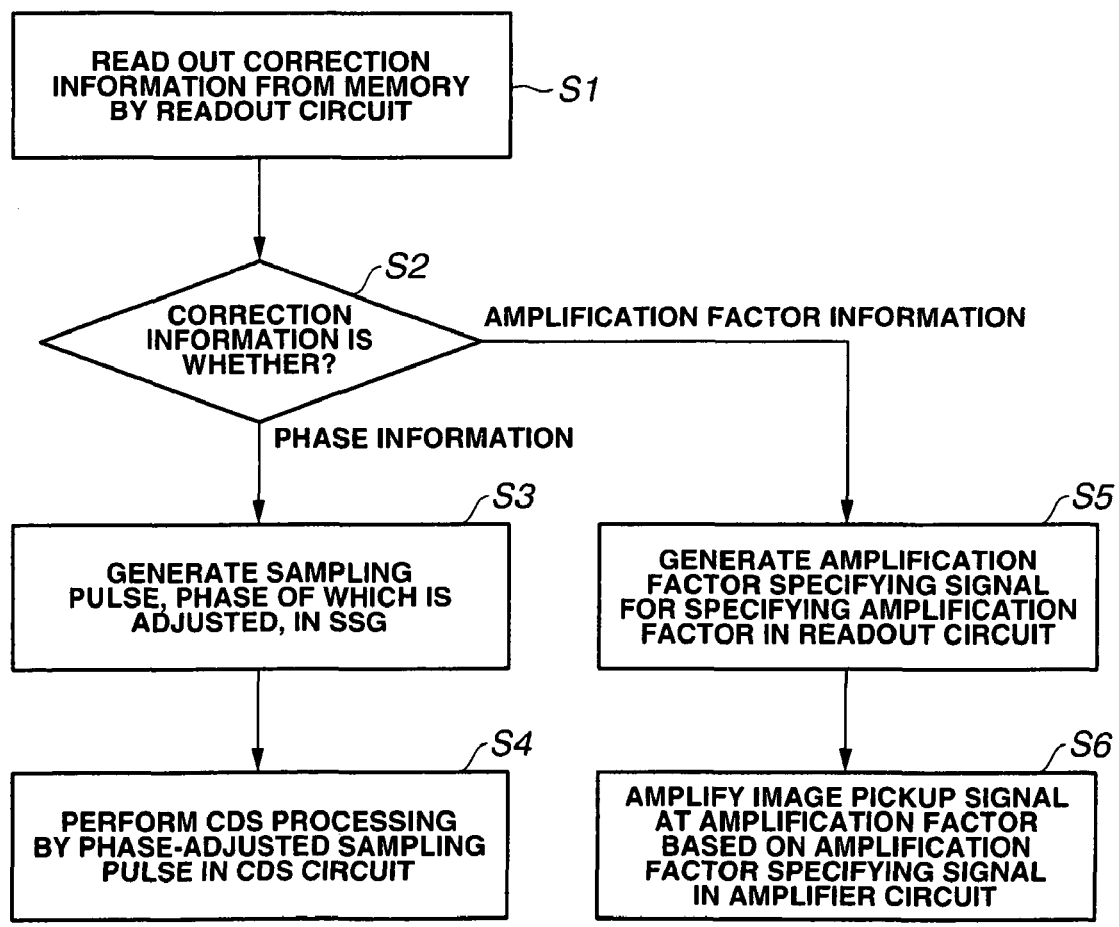
FIG. 3 is a flowchart showing a flow of processing by the video processor of FIG. 2.

As shown in FIG. 3, the video processor 5 reads out the correction information stored in the memory 115 using the readout circuit 114 in step S1.

Then the video processor 5, in step S2, determines whether the correction information read out by the readout circuit 114 is the amplification factor information or phase information.

When determining that the read-out correction information is the phase information, in step S3, the video processor 5 generates sampling pulses the phase of which are corrected based on the phase information in the SSG 113 and outputs the phase-corrected sampling pulses to the CDS circuit 102. In step S4, the video processor 5 causes the CDS circuit 102 to perform the CDS processing using the phase-corrected sampling pulses. That is, in the CDS circuit 102 as a sampling section for sampling the image pickup signal, the phases of the sampling pulses are set based on the correction information stored in the memory 115.

On the other hand, when determining that the correction information read out by the readout circuit 114 is the amplification factor information, in step S5, the video processor 5 generates an amplification factor specifying signal as a serial signal for specifying the amplification factor of the amplifier section 101 based on the amplification factor information, and outputs the amplification factor specifying signal to the amplifier circuit 101. Then in step S6, the video processor 5 amplifies the image pickup signal at the amplification factor based on the amplification factor specifying signal in the amplifier circuit 101.

That is, the correction section including the SSG 113 and the memory 115 electrically corrects the image pickup signal which is signal-processed in the preceding-stage signal processing circuit 51 based on the correction information stored in the memory 115.

(Effect)

Thus, in the present embodiment, the amplification factor information (how much the image pickup signal should be attenuated) among the correction information from the memory 115 is fed to the amplifier circuit 101, and the image pickup signal is amplified to a video signal level with a proper optimal amplification factor. Furthermore, the phase information (how much the phase should be delayed) among the correction information from the memory 115 is fed to the SSG 113, and the sampling pulses (SHP, SHD, ADCLK) having appropriate phases are sent from the SSG 113 to the CDS circuit 102, and thereby optimal correlated double sampling is performed.

Accordingly, the present embodiment enables the optimal processing of the image pickup signal, which has been conventionally performed with a large-scale circuit, with a simple configuration while ensuring space savings.

Note that the amplification factor of the amplifier circuit 101 and the phases of the sampling pulses to be used in the CDS circuit 102 are set based on the correction information stored in the memory 115 in the above-described present embodiment. However, the drive signal of the driving circuit 100 may be electrically corrected.

Modified Example

Next, modified examples of the first embodiment will be described. Note that description of the same components as those in the first embodiment will be omitted, and only the different points will be described.

First Modified Example

In recent years, the loss of frequency of a transmission cable has become higher due to the reduction in diameter of endoscopes. In addition to that, the frequency rate has become higher with the improvement in image quality. As a result, the waveform of the image pickup signal after passing through the transmission cable becomes very dull, which significantly reduces the phase margin of correlated double sampling.

To address this problem, a frequency correction device 121 is provided on an input side of the transmission path 22 for transmitting signals as the first modified example of the present embodiment, as shown in FIG. 4. By providing the frequency correction device 121 as such, the characteristics of the transmission cables having different lengths are corrected based on the characteristic of the frequency correction device corresponding to the characteristic of each of the cables such that the cables as the transmission path 22 have the same overall characteristic, as shown in FIGS. 5 and 6. The frequency correction device 121 can be configured of a resistor and a capacitor connected in parallel with each other, for example, and can provide a great effect with a reduced space.

As described above, the frequency correction device 121 corrects the frequency of the image pickup signal which is transmitted through the transmission path 22, according to the signal transmission characteristic of the transmission path 22. The transmission path 22 transmits the image pickup signal corrected by the frequency correction device 121.

Note that the frequency correction device may be provided in the driving circuit 100. In that case, the frequency correction device corrects the frequency of the drive signal which is transmitted through the transmission path 22 for transmitting the drive signal, according to the signal transmission characteristic of the transmission path 22 for transmitting the drive signal. The transmission path for transmitting the drive signal transmits the drive signal corrected by the frequency correction device.

Second Modified Example

In the present embodiment, the correction information corresponding to the transmission path 22 is stored in advance in the memory. However, there is no limitation placed thereon. For example, as shown in FIG. 7 as the second modified example, an ID information storage section 122 in which ID information for identifying the type of the endoscope may be provided inside of the connector of the endoscope 2 which is connected to the video processor 5, and correction information based on the ID information may be downloaded into the memory 115 from a recording medium not shown.

In this case, correction information corresponding to the ID information of various types of endoscopes used as the endoscope 2 is previously downloaded into the memory 115 of the video processor 5 from the recording medium not shown. When the endoscope 2 is connected to the video processor 5, the readout circuit 114 reads out the ID information of the endoscope 2 from the ID information storage section 122, and reads out the correction information from the memory 115 based on the ID information.

In the video processor 5 according to the second modified example, the correction information corresponding to the ID information of the various types of endoscopes used as the endoscope 2 is previously downloaded in the memory 115. When the endoscope 2 is connected to the video processor 5, the ID information of the endoscope 2 can be read out from the ID information storage section 122 and the correction information can be read out from the memory 115 based on the ID information. Even if the various types of endoscopes used as the endoscope 2 are selectively connected to the video processor 5, optimal processing of the image pickup signal can be performed in the video processor 5 with a simple configuration, while ensuring space savings.

Second Embodiment

Figure 11:
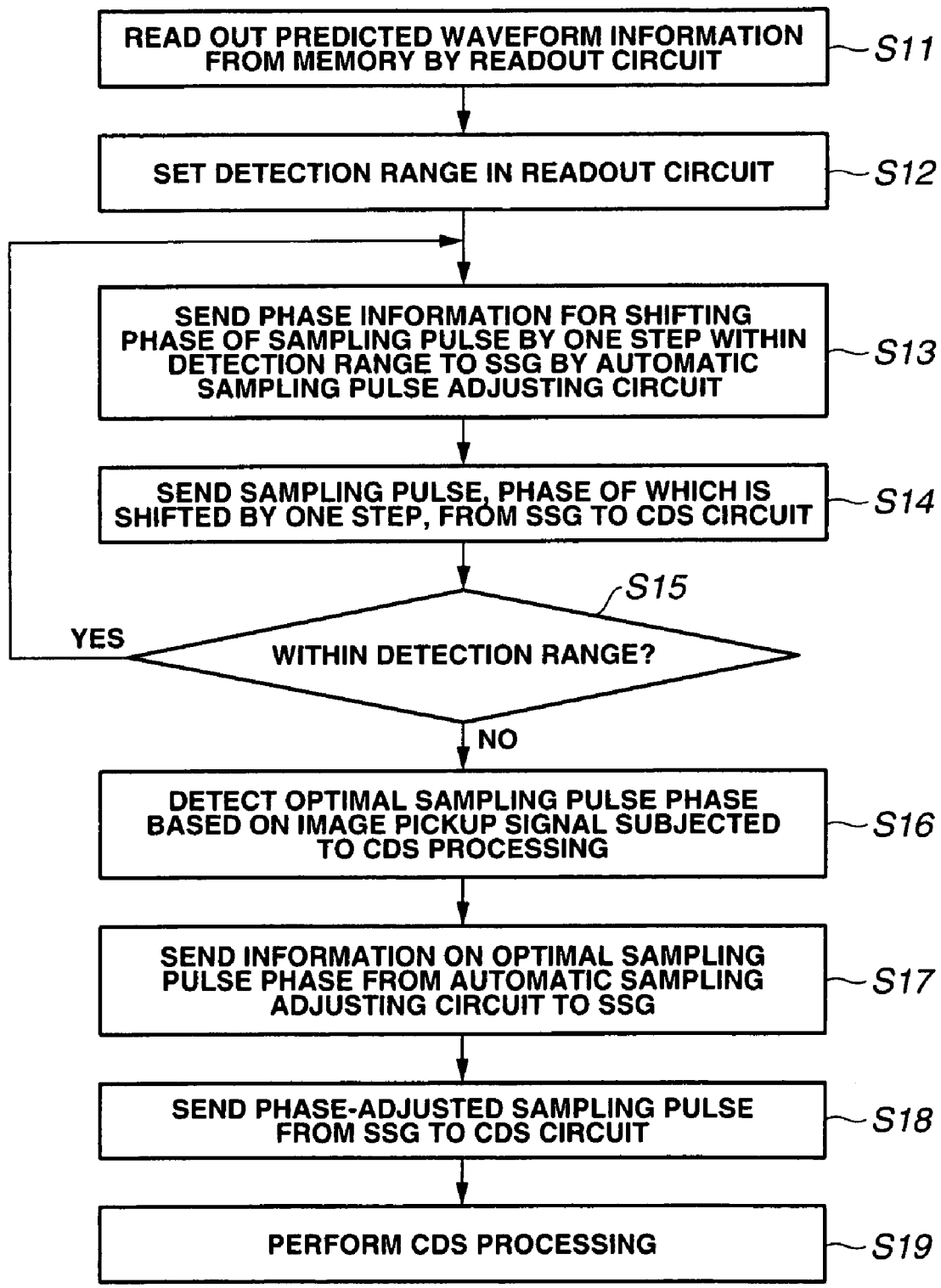
FIG. 11 is a flowchart showing a flow of processing by the video processor of FIG. 8.

FIGS. 8 to 11 relate to the second embodiment of the present invention. FIG. 8 is a block diagram showing a configuration of the video processor. FIGS. 9A to 9C are first views for describing a working of the video processor of FIG. 8. FIG. 10 is a second view showing the working of the video processor of FIG. 8. FIG. 11 is a flowchart showing a flow of processing by the video processor of FIG. 8.

Since the configurations of the second embodiment are almost the same as those of the first embodiment, only the different points will be described. The same components are attached with the same reference numerals and description thereof will be omitted.

(Configuration)

As shown in FIG. 8, the video processor 5 according to the present embodiment is configured by including an automatic sampling pulse adjusting circuit 130 that generates phase information for adjusting the phase difference of the sampling pulses (SHP, SHD) to be used in the CDS circuit 102 and sends the generated phase information to the SSG 113. Other configurations are the same as those of the first embodiment. Note that, in the present embodiment, information on a predicted waveform as an approximate waveform of the image pickup signal for each product type of the endoscope 2 is stored in the memory 115.

Conventionally, the sampling pulses have been applied to the image pickup signal as a whole and the phase difference in the sampling pulses (SHP, SHD) in the CDS circuit 102 has been adjusted. In the case of using such an automatic sampling pulse adjustment for detecting the image pickup signal, sometimes noise is falsely detected by detecting the image pickup signal at wrong detection positions and sampling is performed at noise positions, as shown in FIG. 9A to 9C. As a result, stable image quality cannot be obtained in some cases.

In order to address such a problem, the present embodiment has the memory 115 to prestore information on the predicted waveform which is an approximate waveform of an image pickup signal for each product type of endoscope 2 as shown in FIG. 10, so that phases of the sampling pulses are adjusted within a certain range.

(Working)

In the present embodiment, as shown in FIG. 11, the video processor 5 reads out the predicted waveform information from the memory 115 by using the readout circuit 114 in step S11. Then in step S12, the video processor 5 sets in the readout circuit 114 detection ranges within which the phases of sampling pulses are adjusted.

Next, in step S13, the video processor 5 generates phase information for shifting the phases of the sampling pulses by one step within the set detection ranges and transmits the generated phase information to the SSG 113 by using the automatic sampling pulse adjusting circuit 130. Then in step S14, the video processor 5 transmits the sampling pulses the phases of which are shifted by one step, from the SSG 113 to the CDS circuit 102.

Next, in step S15, the video processor 5 determines whether or not the phases of the sampling pulses are within the detection ranges in the automatic sampling pulse adjusting circuit 130. When the phases of the sampling pulse are within the detection ranges, the video processor 5 repeats the processing in step S13 and S14. When the phases of the sampling pulses exceed the detection ranges, the processing proceeds to step S16.

In the step S16, the video processor 5, detects the optimal sampling pulse phase by using the automatic sampling pulse adjusting circuit 130 based on the image pickup signal subjected to the CDS processing in the CDS circuit 102.

Subsequently, in the step S17, the video processor 5 transmits the information on the optimal sampling pulse phase to the SSG 113 by the automatic sampling pulse adjusting circuit 130.

Next, in step S18, the video processor 5 transmits the sampling pulses the phases of which have been adjusted (corrected) based on the information on the optimal sampling pulse phase from the SSG 113 to the CDS circuit 102. That is, the detection position of the sampling pulses to be used in the CDS circuit 102 is set based on the correction value stored in the memory 115.

After that, in step S119, the video processor 5 performs CDS processing in the CDS circuit 102 by the phase-adjusted (corrected) sampling pulses.

As described above, the memory 115 stores the previously set detection range of the sampling pulses as the correction value, and the detection positions are set within the detection range.

(Effect)

In the present embodiment, in addition to the effect of the first embodiment, the phase of the sampling pulse is adjusted within a certain range based on the predicted waveform information, thereby preventing large shift of sampling timing due to false detection of noise.

Each of the embodiments and modified examples of the present invention can provide the effect that, using a simple configuration, signals can be transmitted by the appropriate characteristic in accordance with the type and characteristic of each endoscope.

The present invention is not limited to the two embodiments and modified examples thereof, and various changes and modifications are possible without changing the gist of the present invention.

What is claimed is:

1. An image pickup system comprising:
   an image pickup section including an image pickup device for picking up an image of a subject;
   a signal processing section for signal-processing an image pickup signal outputted from the image pickup device;
   a transmission path for transmitting the image pickup signal from the image pickup device to the signal processing section;
   a storage section for storing a correction value corresponding to a characteristic of the image pickup device or a characteristic of the transmission path, the correction value including amplification factor information for an amplifier circuit which amplifies the image pickup signal and phase information for correction of phases of sampling pulses of a correlated double sampling circuit which performs correlated double sampling processing on the image pickup signal; and
   a correction section for amplifying the image pickup signal which is signal-processed in the signal processing section, based on the amplification factor information included in the correction value stored in the storage section, and correcting the phases of the sampling pulses of the correlated double sampling circuit, based on the phase information included in the correction value.

2. The image pickup system according to claim 1, further comprising
   a frequency correction device for correcting a frequency of the image pickup signal which is transmitted through the transmission path, according to a signal transmission characteristic of the transmission path, wherein
   the transmission path transmits the image pickup signal corrected by the frequency correction device.

3. The image pickup system according to claim 1, wherein the image pickup section is arranged at a distal end of an insertion portion of an endoscope, the insertion portion being inserted into a lumen.

4. An image pickup system comprising:
   an image pickup section including an image pickup device for picking up an image of a subject;
   a driving section for generating a drive signal for driving the image pickup device;
   a signal processing section for signal-processing an image pickup signal outputted from the image pickup device;
   a drive signal transmission path for transmitting the drive signal to the image pickup section;
   an image pickup signal transmission path for transmitting an image pickup signal from the image pickup device to the signal processing section;
   a storage section for storing a first correction value corresponding to a characteristic of the image pickup device, or a characteristic of the image pickup signal transmission path, and a second correction value corresponding to a characteristic of the drive signal transmission path, the first correction value including amplification factor information for an amplifier circuit which amplifies the image pickup signal and phase information for correction of phases of sampling pulses of a correlated double sampling circuit which performs correlated double sampling processing on the image pickup signal; and
   a correction section for amplifying the image pickup signal which is signal-processed in the signal processing section based on the first correction value stored in the storage section, and correcting the phases of the sampling pulses of the correlated double sampling circuit based on the phase information included in the first correction value, and further correcting the drive signal based on the second correction value stored in the storage section.

5. The image pickup system according to claim 4, further comprising
   a frequency correction device for correcting a frequency of the drive signal which is transmitted through the drive signal transmission path or of the image pickup signal which is transmitted through the image pickup signal transmission path, according to a signal transmission characteristic of the drive signal transmission path or of the image pickup signal transmission path, wherein
   the drive signal transmission path or the image pickup signal transmission path transmits the drive signal corrected by the frequency correction device or the image pickup signal corrected by the frequency correction device.

6. The image pickup system according to claim 4, wherein the image pickup section is arranged at a distal end of an insertion portion of an endoscope, the insertion portion being inserted into a lumen.

7. An image pickup system comprising:
- a signal processing section for signal-processing an image pickup signal outputted from an image pickup device for picking up an image of a subject;
- a transmission path for transmitting the image pickup signal from the image pickup device to the signal processing section;
- a storage section for storing a correction value corresponding to a characteristic of the image pickup device or a characteristic of the transmission path, the correction value including amplification factor information for an amplifier circuit which amplifies the image pickup signal and phase information for correction of phases of sampling pulses of a correlated double sampling circuit which performs correlated double sampling processing on the image pickup signal; and
- a correction section for amplifying the image pickup signal which is signal-processed in the signal processing section, based on the amplification factor information included in the correction value stored in the storage section, and correcting the phases of the sampling pulses of the correlated double sampling circuit, based on the phase information included in the correction value.

8. The image pickup system according to claim 7, further comprising
- a frequency correction device for correcting a frequency of the image pickup signal which is transmitted through the transmission path, according to a signal transmission characteristic of the transmission path, wherein
- the transmission path transmits the image pickup signal corrected by the frequency correction device.

9. The image pickup system according to claim 7, wherein the image pickup section is arranged at a distal end of an insertion portion of an endoscope, the insertion portion being inserted into a lumen.

* * * * *